United States Patent [19]

Miyazaki

[11] Patent Number: 4,919,114
[45] Date of Patent: Apr. 24, 1990

[54] ENDOSCOPE PROVIDED WITH FLEXIBLE SIGNAL WIRES

[75] Inventor: Atsushi Miyazaki, Hachioji, Japan

[73] Assignee: Olympus Optical Co., Ltd., Tokyo, Japan

[21] Appl. No.: 294,437

[22] Filed: Jan. 9, 1989

[30] Foreign Application Priority Data

Jan. 14, 1988 [JP] Japan ................................ 63-005925

[51] Int. Cl.$^5$ ............................................... A61B 1/04
[52] U.S. Cl. ............................................ 128/6; 358/98
[58] Field of Search ........................ 128/4, 6; 358/98

[56] References Cited

U.S. PATENT DOCUMENTS 4,607,621 8/1986 Wheeler .................................. 128/6

FOREIGN PATENT DOCUMENTS 60-83640 5/1985 Japan .
62-42610 9/1987 Japan .

Primary Examiner—William H. Grieb
Attorney, Agent, or Firm—Armstrong, Nikaido, Marmelstein, Kubovcik & Murray

[57] ABSTRACT

The endoscope of the present invention, in which the flexibility of a part of a signal wire inserted through the insertable part is varied, is provided with a flexible insertable part to be inserted into a body cavity. A solid state imaging device obtains an optical image of an observed part through an observing window provided in the tip part of the insertable part. A signal wire inserted through the above mentioned insertable part, is electrically connected to the above mentioned solid state imaging device and has parts with different flexibility.

7 Claims, 9 Drawing Sheets

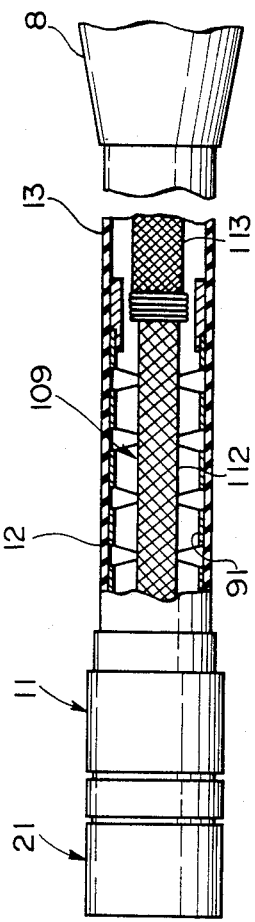
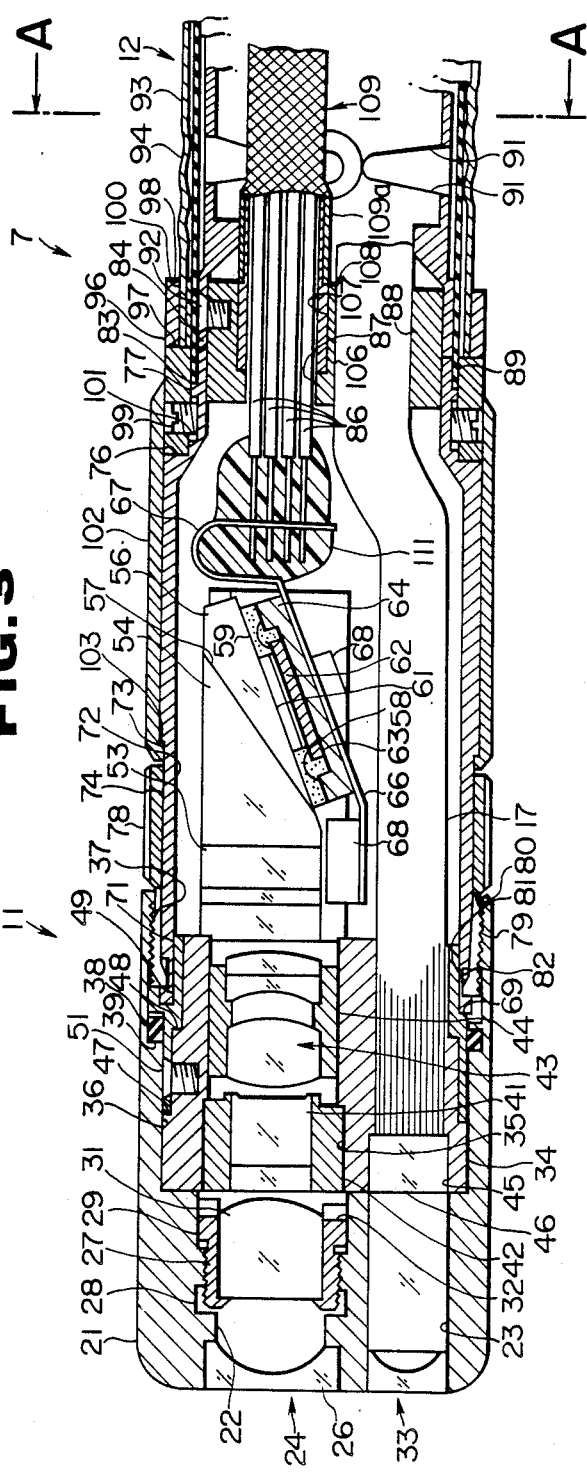
FIG.2
FIG.3

FIG. 7
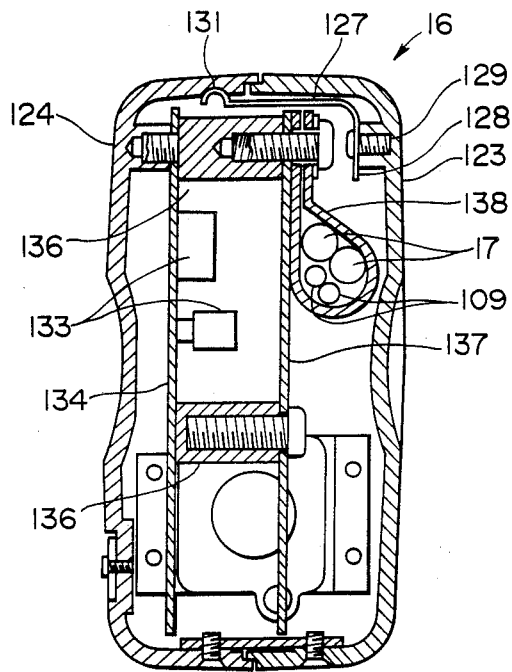
FIG. 8(a) FIG. 8(b)
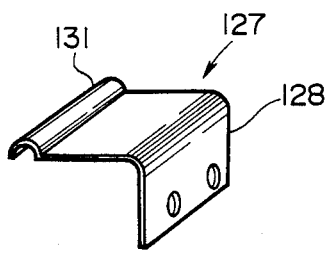 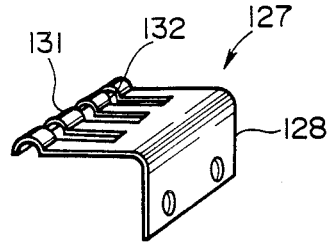

ENDOSCOPE PROVIDED WITH FLEXIBLE SIGNAL WIRES

FIELD AND BACKGROUND OF THE INVENTION

This invention relates to an endoscope wherein the flexibility of a part of signal wires, inserted through the insertable part, is varied.

Recently, there has come to be extensively used an endoscope (scope or fiber scope) whereby organs within a body cavity and the like can be diagnosed or inspected by inserting an elongate insertable part into the body cavity.

It is used not only for medical uses but also for industrial uses in observing and inspecting objects such as boilers, machines and interiors of pipes and machines of chemical plants.

Further, there are used various kinds of electronic scopes wherein a solid state imaging device as a charge coupled device (CCD) is used as an imaging means. The electronic scope advantages are that the resolution is higher and it is easier to record, reproduce, enlarge and compare picture images than in a fiber scope.

On the signal wire, connected to the solid state imaging device and transmitting driving signals or output signals, a shielding technique as a countermeasure of reducing emitted noises is disclosed in the publications of Japanese patent application publication No. 42610/1987 and Japanese patent application laid open No. 83640/1985.

In the publication of the above mentioned Japanese patent application publication No. 42610/1987, a signal wire from a solid state imaging device contained in an X-ray shielding body made of a metal is coated with a shielding wire which is electrically connected to the X-ray shielding body to prevent defects such as an operation failure and picture image disturbance from being caused even under the sight with X-rays. In the publication of the above mentioned Japanese patent laid open No. 83640/1985, a signal wire is shielded to prevent picture image noises when using a high frequency treating tool.

Now, shielding the entire signal wire is advantageous not only to the above but also to preventing noises emitted from the signal wire. In order to further elevate this preventing effect, it is effective to elevate the shielding density. However, if the shielding density is made high, the rigidity of the signal wire will become high and the curving operation of the endoscope insertable part through which this signal wire high in rigidity is inserted will be obstructed. On the other hand, if the shielding density is made low to improve the curving operability, noises will not be able to be prevented from being mixed in or discharged out.

SUMMARY AND OBJECT OF THE INVENTION

An object of the present invention is to provide an endoscope wherein, without reducing the curving operability of the curvable part or the flexibility on the insertable part tip side, noise can be prevented from being mixed in or discharged out.

The endoscope according to the present invention has a flexible insertable part to be inserted into a body cavity and is provided with an observing window in the tip part of the insertable part. The insertable part is provided with a solid state imaging device obtaining an optical image of an observed part through the observing window and signal wires inserted through the above mentioned insertable part, electrically connected to the above mentioned solid state imaging device and having parts with different flexibility.

BRIEF DESCRIPTION OF THE DRAWINGS

FIGS. 1 to 8 relate to the first embodiment of the present invention.

FIG. 1 is an explanatory view of the whole of an endoscope apparatus.

FIG. 2 is an explanatory view of signal wires inserted through the insertable part.

FIG. 3 is a sectioned view of a tip part provided with a tip adapter.

FIG. 4 is a sectioned view in the direction A—A in FIG. 3.

FIG. 5 is an explanatory view of a shielding wire within a light source connector part.

FIG. 6 is a sectioned view in the direction B—B in FIG. 5.

FIG. 7 is a sectioned view of a light source connector.

FIG. 8($a$) and FIG. 8($b$) are explanatory views of a conducting plate.

FIG. 9 is a sectioned view of an insertable part.

FIG. 10 is a sectioned view of another insertable part.

FIGS. 11 and 13 are explanatory views of a drum winding type endoscope apparatus fitted with a rotary type visual field converting adapter.

FIG. 11 is a sectioned view showing an endoscope tip part and rotary type visual field converting adapter.

FIG. 12 is a perspective view showing the whole of a drum winding type endoscope apparatus.

FIG. 13 is a side view showing an endoscope apparatus having an operating part.

FIGS. 14 and 15 relate to an endoscope apparatus fitted with an auxiliary light source adapter.

FIG. 14 is a sectioned view showing an endoscope tip part and auxiliary light source adapter.

FIG. 15 is an elevation of an adapter with the cover member in FIG. 4 removed.

DETAILED DESCRIPTION OF PREFERRED EMBODIMENTS OF THE INVENTION

The present invention shall be explained in the following with reference to the drawings.

FIGS. 1 to 8 show the present invention.

Figure 1:
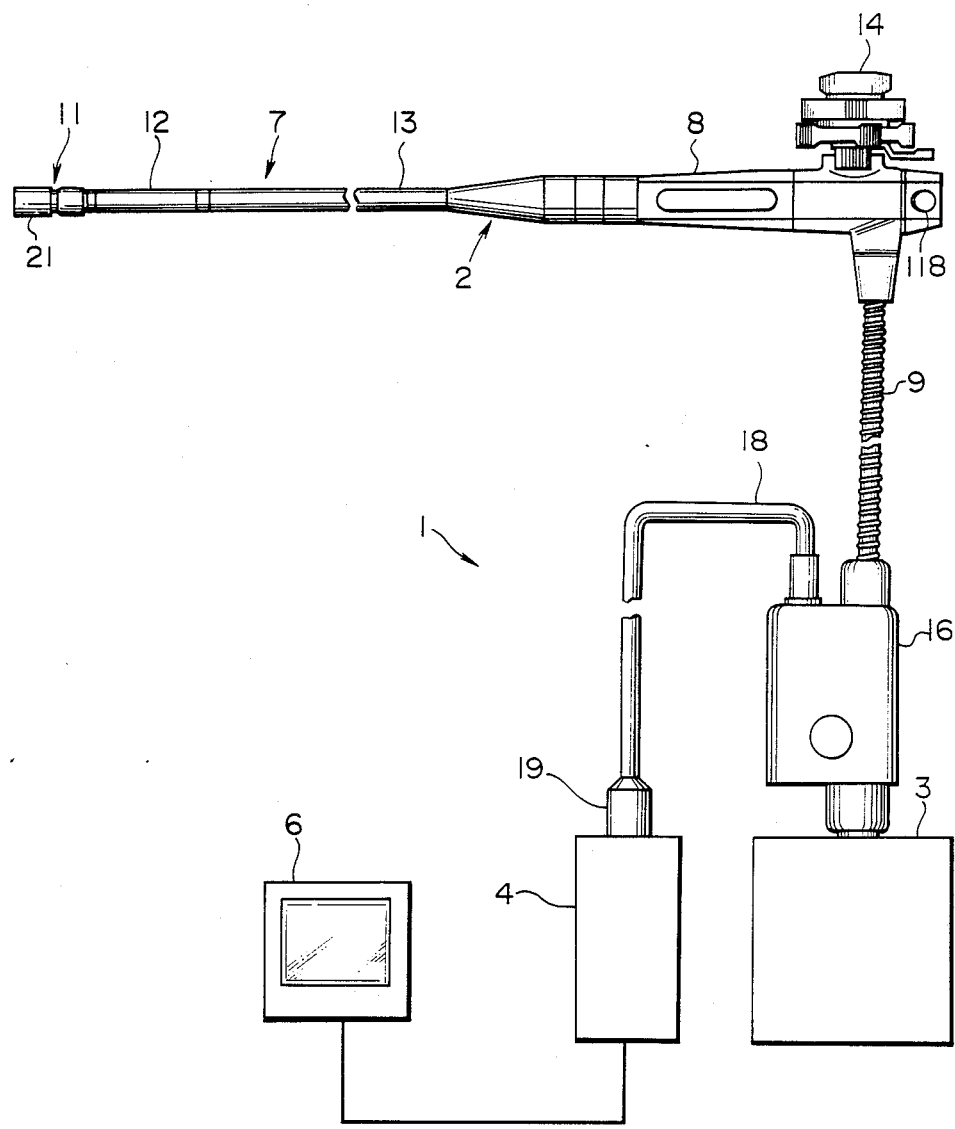

In FIG. 1, an endoscope apparatus 1 comprises an electronic endoscope 2, a light source apparatus 3 feeding an illuminating light to this electronic endoscope 2, a camera controlling unit 4 processing a picture image delivered from the above mentioned electronic endoscope into a video signal and a monitor 6 displaying on a picture surface the video signal output from this camera controlling unit (abbreviated as CCU hereinafter).

The above mentioned electronic endoscope 2 is provided with an elongate insertable part 7, a thick operating part 8 connected to the rear end side of this insertable part and a light guide hose 9 extended from the side of the above mentioned operating part 8.

The above mentioned insertable part 7 is provided on the tip side with a rigid tip part 11, on the rear side adjacent to this tip part 11 with a curvable part 12 which can be curved and further in the rear of this curvable part 12 with a flexible soft part 13. The above mentioned curvable part 12 can be curved in the vertical and horizontal directions by operating a curving operation knob provided on the above mentioned operating part 8.

A light source connector part 16 is provided at the rear end of the above mentioned light guide hose 9 and is connected to the light source apparatus 3 so that an illuminating light emitted from a light source lamp not illustrated provided within the light source apparatus 3 may be fed to a light guide entrance end surface not illustrated.

A signal cable 18 is extended from the end of the above mentioned light source connector part 16 and a signal connector 19 provided at the rear end of this signal cable 18 is connected to the above mentioned CCU 4 which is connected to the monitor 6 which can display an observed image.

In FIG. 3, the above mentioned tip part 11 is provided with a tip optical adapter 21 as an adapter formed to be substantially columnar of a rigid material. On the front end surface of this tip optical adapter 21, an observing through hole 22 and illuminating light through hole 23 are formed parallelly with the lengthwise direction of the insertable part 7.

A first lens 26 forming a picture angle changing lens system 24 is fitted at the front end of the above mentioned observing through hole 22 and a second lens 31 fitted in a lens frame 29 having a male screw part 28 screwed to a female screw part 27 provided on the inner periphery of the observing through hole 22 and forming the picture angle changing lens system 24 is provided movably in the lengthwise direction and is fitted in the rear of the first lens 26. A plurality of grooves 32 are made in the diametrical direction on the rear end surface of the above mentioned lens frame 29 so as to act as engaging parts in rotating the lens frame 29, for example, with a jig.

A light distributing lens system 33 is fitted and fixed within the above mentioned illuminating through hole 23.

A circular recess 36 into which a tip part body 34 can be inserted, where the tip part body 34 is provided in the above mentioned tip part 11 and formed to be substantially columnar of a rigid material such as a metal the annular recess 36 is provided on the rear end surface of the tip optical adapter 21 so that the center lines of the tip optical adapter 21 and insertable part may coincide with each other.

A screw 37 is threaded at the end of the inner peripheral surface of the above mentioned recess 36. A groove 39, in which an annular water-tight member 38 such as an 0-ring is inserted, is provided on the inner peripheral surface in front of the above mentioned screw 37.

The tip part body 34 inserted into the above mentioned recess 36 is provided with an observing through hole 35 and illuminating through hole 45 parallelly with the lengthwise direction of the insertable part 7.

An optical rod 41, a first lens frame 42 and a second lens frame 44 having an objective lens system 43 internally fitted in the rear of this first lens frame are fitted and positioned in the above mentioned observing through hole 35.

A cover glass 46 is contained in the above mentioned illuminating through hole 45 at the front end. The light guide 17 inserted through the insertable part 7 contacts on the end surface with the above mentioned cover glass 46 on the rear end surface.

Steps 47 and 48 are formed so as to be of a diameter smaller toward the rear end part in the rear Part of the outer periphery of the tip part body 34. A cylindrical prism frame 49 contacts on the front end surface with the above mentioned step 47, is fitted into the tip part body 34 with the outside diameter coinciding with the outside diameter of the tip part body 34 and is fixed to the tip part body 34 with a plurality of screws 51.

In the rear end part of the above mentioned prism frame 49, a square pillar-like optical low pass filter 53, a first prism 54 as a light leading means and a second prism 56 are held in order from the tip side.

The above mentioned optical low pass filter 53 is arranged so that the front end surface and rear end surface may be vertical to the optical axis of the above mentioned objective lens system 43. The front end surface of the above mentioned first prism 54 is secured to the rear end surface of this optical low pass filter 53. A slope 57 is formed on the rear end side of this first prism 54. On the other hand, the above mentioned second prism 56 is formed to be wedge-like and is secured on the front end surface to the slope 57 so that the thin part may be on the tip side. The rear end surface 58 of this second prism 56 is inclined to the lengthwise direction of the above mentioned insertable part 7. A sealing glass 61 provided on the imaging surface side of a solid state imaging package 59 contacts the above mentioned rear end surface 58 and is arranged on the above mentioned second prism 56 so as to incline to the lengthwise direction of the insertable part 7. An interfering filter 62 such as a color filter array is formed on the rear end surface of this sealing glass 61. Further, a solid state imaging chip 63 is overlapped on this rear end surface and is secured to a package base 64 formed of such material as ceramics and is sealed with a sealing resin.

A substrate 66 is fitted on the opposite imaging surface side of the above mentioned solid state imaging package 59. The solid state imaging package 59 and/or substrate 66 is secured to the above mentioned prism frame 49 such as by cementing.

On the rear end side of the above mentioned substrate 66, a core wire connecting part 67 is extended as bent so that the solid state imaging package 59 fitting side may be directed rearward. Electronic parts 68 are fitted on the substrate 66 extended to the front end side and on the back surface of the substrate 55.

On the outer peripheral surface of the rear part of the above mentioned prism frame 49, a step 69 is provided and a small diameter part 71 is formed. In this small diameter part 71, a cover member 72 formed to be substantially cylindrical of rigid material such as a metal and capable of housing the above mentioned substrate 66 is secured on the front end surface in contact with the above mentioned step 69. A small diameter part 74 thinner forward is formed by a step 73 in the front part of the outer peripheral surface of the above mentioned cover member 72 and a small diameter part 77 thinner rearward is formed by a step 76 in the rear part.

On the outer peripheral surface of the above mentioned front small diameter part 74, a connecting ring 78 having the same outside diameter as the outside diameter of the above mentioned tip optical adapter 21 is inserted so as to be rotatable on the outer peripheral surface of the above mentioned small diameter part 74. On the outer peripheral surface of the front part of the above mentioned connecting ring 78, a screw 79 having a plurality of slits 80 in the lengthwise direction is threaded and provided so as to be able to be screwed with the screw 37 provided on the inner peripheral surface at the rear end of the above mentioned tip optical adapter 21. Also, on the inner peripheral surface of the front part of the connecting ring 78, a projection 81 is provided so as to be engageable with a recess 82 provided on the outer peripheral surface of the front part of the above mentioned cover member 72.

In the small diameter part 77 in the rear part of the above mentioned cover member 72, further a small diameter part 84 smaller rearward is formed by a step 83.

In the inside diameter of the rear part of the above mentioned cover member 72, a columnar ring retainer 89 having a core wire through hole 87 through which a plurality of core wires 86 forming a shielding wire 109 connected to the above mentioned core wire connecting part 67 pass and a light guide through hole 88 is fitted and fixed so as to expose a part of the outer peripheral surface.

An articulate frame 91 at the foremost end of many substantially annular articulate frames 91 connected in the lengthwise direction within the insertable part 7 so as to be rotatable within the curvable part 12 is externally fitted to the exposed part of the above mentioned ring retainer 89 and is fixed to the ring retainer 89 with a screw 92.

The above mentioned articulate frame 91 is coated with a flexible tube member 93 which is externally fitted at the front end to the small diameter part 84 so as to contact the above mentioned step 83. Further, the above mentioned tube member 93 is coated on the outer periphery with a protective sheath 94 made of a net tube or the like made by knitting such fine wires as of a metal to be like a net.

The above mentioned protective sheath 94 is externally fitted at the front end to a small diameter part 100 formed by a step 97 in the rear of a cylindrical fixing member 96 having an outside diameter equal to or smaller than the outside diameter of the above mentioned cover member 72 and contacts on the front end surface with the above mentioned step 97.

The protective sheath 94 externally fitted to the above mentioned fixing member 96 is externally fitted on the outer periphery of the front end part with a cylindrical stopper having the same outside diameter as the outside diameter of the fixing member 96 to secure the fixing member 96 and protective sheath 94 by a fixing means such as soldering.

In the front part of the above mentioned fixing member 96, a plurality of screws 99 are screwed in the diametrical direction through the inner peripheral surface and contact and press at the tips a recess 101 provided in the small diameter part 77 of the above mentioned cover member 72 to connect the protective sheath 94 and tip part 11 with each other.

A cylindrical drop preventing member 102 is loosely fitted to the above mentioned cover member 72 on the outer periphery and fixing member 96 on the outer periphery including the screw 99 to prevent the screw 99 from dropping, is of the same outside diameter as the outside diameter of the tip optical adapter 21 and is provided on the front part of the inner peripheral surface with a step 103 to contact the step 73 provided on the above mentioned cover member 72.

In the rear part of the above mentioned core wire through hole 87, an expanded diameter part 107 is formed by a step 106 and a tubular electric wire retainer 108 having the same inside diameter as that of the core wire through hole 87 and smaller in diameter in the rear part is fitted and fixed in the above mentioned expanded diameter part 107.

In the small diameter part of the above mentioned electric wire retainer 108, an external conductor 109a coating the core wires 86 on the outer periphery is expanded in diameter, is externally fitted, is fixed by soldering or with a conductive cementing agent and is fixed as kept electrically conductive with the metal parts of the light source connector part 16 and CCU 4.

The above mentioned core wires 86 are inserted through the electric wire retainer 108, are connected to the core wire connecting part 67, are coated in the core wire connecting part 67 and its vicinity with a reinforcing member 111 such as a cementing agent, are fixed and re secured to the electric wire retainer 108 with an insulating cementing agent or the like. The external conductor 109a is fixed so that the electric wire retainer 108, cover member 72 and tip part body 34 may be kept conductive.

Figure 4:
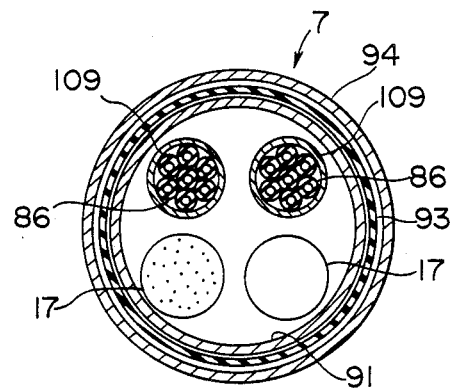

As in FIG. 4, two shielding wires 109 coated, for example, with the external conductor 109a are inserted to the light source connector part 16 through the insertable part 7, operating part 8 and light guide hose part 9.

In FIG. 2, the external conductor 109a is made by knitting, to be like a net fine wires formed of conductive material such as a metal and is formed to be a one-layer external conductor part 112 knitted to be in one layer and having a curvability within the curvable part 12 and to be a two-layer external conductor part 113 knitted to be in two layers within the flexible part 13 in the rear of the curvable part 12 This two-layer external conductor part 113 is fixed in the tip part to the core wires 86 by a fixing means such as a bobbin near the rear part of the curvable part 12 and leads at the rear end to the light source connector part 16.

Figure 5:
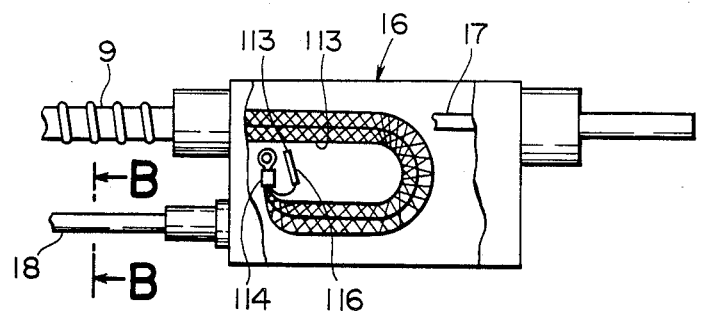

In FIG. 5, the two-layer external conductor part 113 inserted through the light source connector part 12 is separated from the core wires 86 is looped and is then electrically connected to the light source connector part 16 through a pressed terminal provided in the tip part. A conductive cable 116 is connected at one end to this two-layer external conductor part 113 in the position very close to the light guide hose 9 by a connecting means such as soldering and at the other end electrically to the above mentioned pressed terminal 114. Instead of connecting the conductive cable 116 directly with the two-layer external conductor part, the two-layer external conductor part 113 may be coated on the outer periphery with a pipe or coil and the conductive cable 116 may be connected to this pipe or coil.

Figure 6:
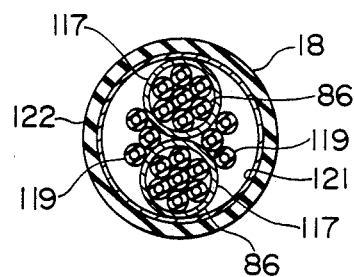

As in FIG. 6, the plurality of core wires 86 separated from the above mentioned two-layer external conductor part are inserted through the above mentioned signal cable 18 extended to the side of the light source connector part 16, are connected to the CCU 4 through the above mentioned signal connector 19, are bundled into two bundles, are coated with external conductors 117 and are further coated with an external conductor 121 together with a plurality of freezing operation signal wires 119 connected to a freezing switch 118 provided at the rear end of the above mentioned operating part 8 along the outer periphery of the external conductors 117. These freezing operation signal wires 119 are coated with external conductors (not illustrated) and are electrically connected to the CCU 4. The external conductor 121 is coated on the outer periphery with a tube member 122 formed of a resin or the like.

In FIG. 7, the light source connector part 16 is formed of cases A 123 and B 124. Within this case A 123, a conductive plate 127 such as is shown in FIG. 8(a) is provided to be kept positively electrically conductive with the case B 124, is plate-like, is bent at one end to be a flange 128, is fixed in this flange 128 to the case A 123 with a screw 129 and is provided at the other end with a projection 131 so that, in fixing the cases A 123 and B 124, the projection 131 may be in contact with the inner surface of the case B 124 by the energizing force. As in FIG. 8(b), the conductive plate 127 may be provided at the other end with a plurality of slits 132 to make the electric conduction with the case B 124 more positive.

An electric substrate 134 fitted with electric parts 133 is provided within the above mentioned case B 124. The light guide 17 and shielding wires 109 are fixed with a fixing metal piece 138 to a fixing plate 137 overlapped on this electric substrate 134 by a spacer 136.

The operation of the electronic endoscope 2 formed as mentioned above shall be explained.

The insertable part 7 of the endoscope 2 is inserted into a body cavity. In order to observe the body cavity interior, the operator operates the curving operation knob 14 provided on the operating part 8 to curve the curvable part 12 in the vertical and horizontal directions. In such a case, as the shielding wire 109 inserted through the curvable part 12 is formed of the one-layer external conductor part 112 higher in the curvability than the two-layer external conductor part 113 inserted through the flexible part 13, the operator can easily operate the curving operation knob 14. The two-layer external conductor part 113 is inserted through the flexible part 13 which is a part in which, even if the rigidity is high to some extent, the operation will not be obstructed. The two-layer external conductor part 113 in the flexible part 13 is knitted in two layers and is higher in shielding effect than the one-layer external conductor part.

The external conductor 109a covers the core wires 86 within the insertable part 7 and is electrically connected to the cases A 123 and B 124. The core wires 86 inserted through the signal cable 18 are covered with the external conductor 117 electrically connected to the cases A 123 and B 124 and CCU 4 body through the signal connector 19. Further, this external conductor 117 and the freezing operation signal wire 119 are covered with the external conductor 121. Therefore, the entire core wires 86 are covered with the external conductors 109a, 117 and 121 so that radioactive noises may be prevented.

In order to reduce radioactive noises, the entire endoscope may be covered with a metal. Therefore, it is apparent to be advantageous to apply a metal coating to a member (for example, the operating part 8) formed of plastics or the like.

As in this embodiment, in such a part a in which the signal wires may have a higher rigidity than when fixed as the flexible part 13 or light guide hose 9, the shielding density of the shielding wires 109 is made as high as possible and, in such a part in which, if the shielding wire 109 has a rigidity, there will be a problem as the curvable part 12, the shielding density of the shielding wire 109 is kept below a predetermined level so that the operability and durability of the electronic endoscope 2 may be elevated. As the length of the curvable part 12 is shorter than the length of the entire shielding wire 109, the length in which the shielding density must be kept low is so slight that there is no problem at all in preventing noises from being discharged out or mixed in.

In this embodiment, the external conductor 109a inserted through the flexible part 13 forms the two-layer external conductor 113 knitted to be of two layers but may be a shielding wire knitted to be of more than two layers.

Further, a tape-like shielding member may be wound on the signal wire 86.

The second embodiment of the present invention shall be explained in the following.

In the first embodiment, as a means of changing the shielding density, in the flexible part 13, the shielding wire 109 is coated with two or more layers. Now, in this embodiment, the knitting condition is changed.

A plurality of core wires 86 inserted through the curvable part 12 are covered with the external conductor 109a coarsely knitted of fine wires made of a metal so as to have a high curvability. Under the knitting condition changed from the curvable part to the flexible part 13, this external conductor 109a is finely knitted to be high in shielding density.

By forming the external conductor 109 as mentioned above, the two-layer external conductor part 113 is formed as compared with the first embodiment, therefore the operation of further coating the external conductor 109a on the outer periphery of the external conductor 109a can be omitted and the shielding wire 109 can be easily formed.

The shielding wire 109 may be electrically connected to two shielding wires different in shielding density. Further, in case it is difficult to directly electrically connect them, they may be connected through a member formed, for example, to be like a pipe and having a conductivity.

The other formations, operations and effects are the same as in the first embodiment.

According to the above mentioned first and second embodiments, by partly changing the shielding density, without reducing the curving operability of the curvable part, noises can be prevented from being mixed in or discharged out and the shielding effect can be elevated.

In the first embodiment, the external conductor 109a is provided with the one-layer part 112 and two-layer part 113 to vary the flexibility. However, the external conductor 109a may be uniformly coated and the outside diameter of the shielding wire may be changed to vary the flexibility.

FIGS. 9 to 15 show the third embodiment of the present invention.

In an endoscope 141 of this embodiment, an insertable part is provided with a two-step hose part.

Figure 9:
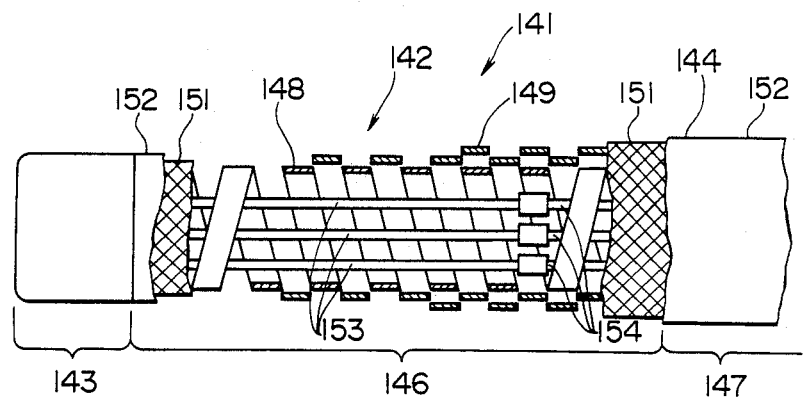
FIGS. 9 to 15 relate to the third embodiment of the present invention.

In FIG. 9, the insertable part 142 of the endoscope 141 comprises a tip part 143, a flexible part 144 provided in the rear of the tip part 143 and an operating part (not illustrated) provided in the rear of this flexible part 144. Further, this flexible part 144 is provided on the tip part side with a first hose part 146 and a second hose part 147 in the rear of this first hose part 146.

The solid state imaging package 59 described in the first embodiment is provided within the above mentioned tip part 143. An inside spiral tube 148 spirally formed of a band-like sheet is connected in the rear of this tip part 143 and is inserted through the flexible part 144. On the outer periphery of the inside spiral tube 148, an outside spiral rube 149 spirally formed of a band-like sheet has its top part positioned at a distance rearward from the connecting part of the above mentioned tip part 143 and inside spiral tube 148, gradually increases the number of layers rearward within the first hose part 146 and has a fixed number of layers within the second hose part 147. Therefore, the first hose part 146 becomes lower in flexibility rearward but the second hose part 147 becomes constant in flexibility.

The above mentioned outside spiral tube 149 is coated on the outer periphery with a net tube 151 knitted of fine wires and further the net tube 151 is coated on the outer periphery with a flexible tube 152.

First shielding wires 153 connected to the above mentioned solid state imaging package 59 are inserted through the first hose part 146, are electrically connected with the second shielding wires 154 inserted through the second hose part 147, are coated with an external conductor not illustrated coarser in the knitting density than in the second shielding wires 154 and are therefore higher in flexibility than the second shielding wires 154.

In this embodiment, no curvable part is provided but the first hose part 146 and second hose part 147 with different flexibility are provided and further first shielding wires 153 within the first hose part 146 are made higher in the flexibility than the second shielding wires to improve the insertability.

The other formations are the same as in the first embodiment.

Figure 10:
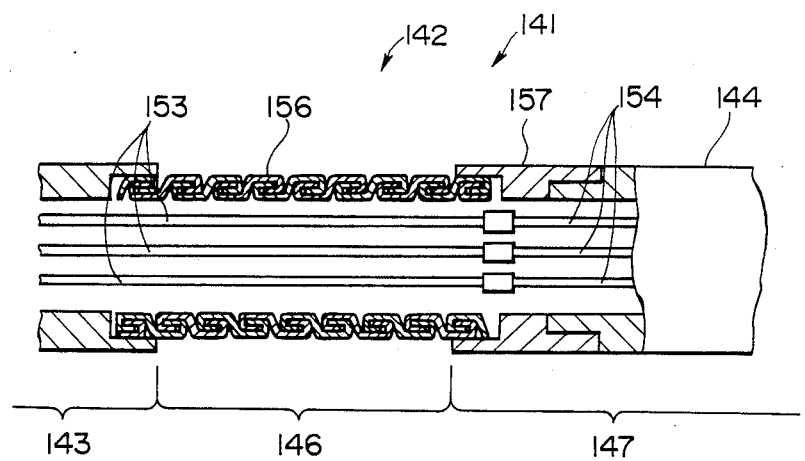

An interlocking type spiral tube such as is shown in FIG. 10 may be used. In FIG. 10, a first hose part 146 connected in the rear of a tip part 143 is formed of an interlocking type spiral rube 156 formed so that the adjacent parts may engage with each other. In the rear of the interlocking type spiral rube 156, a second hose part 147 lower in the flexibility than the first hose part 146 is connected through a hose mouthpiece 157.

The other formations are the same as in FIG. 9.

In FIG. 9 and 10, the shielding wires 53 and 154 with different flexibilities are connected. However, the same shielding wires may be varied in the flexibility in the course by varying the knitting density.

Now, in the above mentioned embodiment, a picture angle converting adapter is fitted to the tip part of the endoscope. However, as in FIGS. 11 and 12, a rotary type visual field converting adapter may be fitted.

Figure 11:
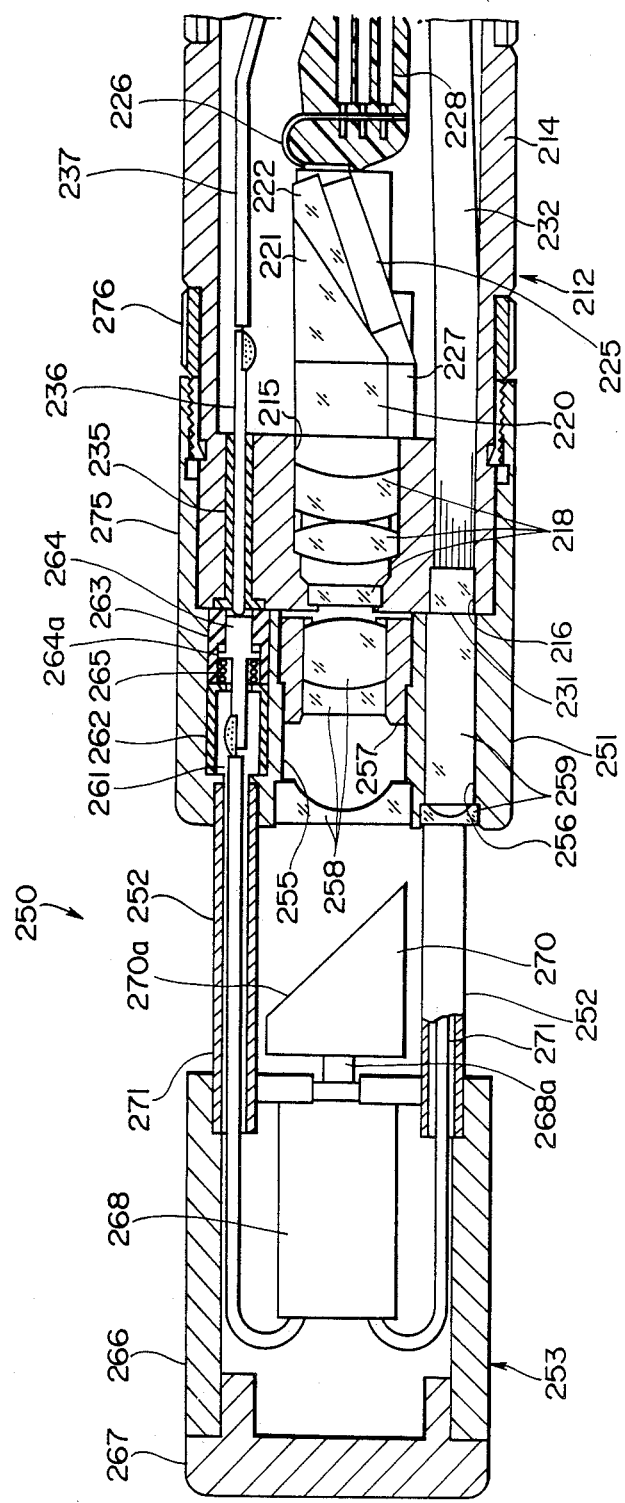
Figure 12:
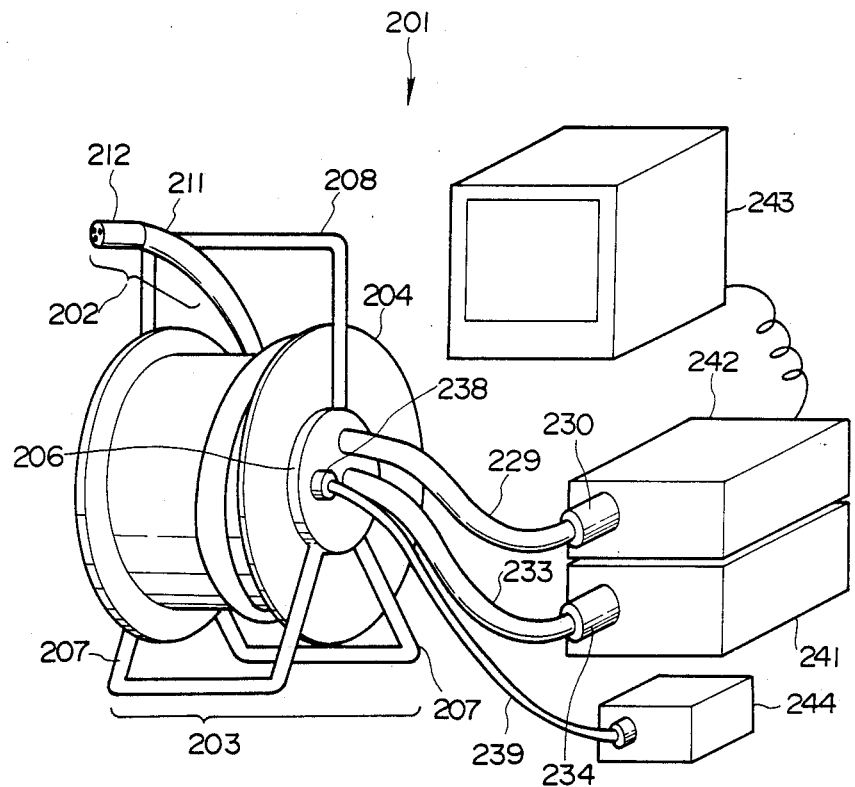

In FIGS. 11 and 12, the rotary type visual field converting adapter shall be explained.

As shown in FIG. 12, an endoscope apparatus 201 is provided with an elongate flexible insertable part 202 and a winding drum unit 203 winding this insertable part 202. The above mentioned insertable part 202 is fixed on the base side to a winding drum 204 or the winding drum unit 203 and is wound and contained in this drum 204. The endoscope apparatus 201 is provided separately from the above mentioned winding drum unit with a light source apparatus 241, a video processor 242, a monitor 243 connected to the above mentioned video processor 242 and a rotation controlling apparatus 244 as an external apparatus.

The above mentioned drum 204 is provided at both ends in the rotary axial direction with rotary shaft parts not illustrated rotatably borne by bearing parts 206. Between both bearing parts, leg-like supporting pipes 207 rotatably supporting the above mentioned drum 204 are provided below and a handle 208 for carrying the drum 204 is mounted above.

The above mentioned insertable part 202 is formed by connecting a rigid tip part 212 to the tip of a flexible tube 211 having a flexibility. A rotary type visual field converting adapter (mentioned as an adapter hereinafter) 250 is removably fitted to the above mentioned tip part on the tip side.

The above mentioned tip part 212 and adapter 250 are formed as shown in FIG. 11.

The above mentioned tip part 212 is provided with a rigid tip part body 214 in which an observing through hole 215 and illuminating through hole 216 are formed parallelly in the lengthwise direction of the insertable part 202. The above mentioned observing through hole 215 is fitted with an objective lens system 218. In the rear end part of the above mentioned tip part body 214, on the above mentioned objective lens system 218, an optical rod 220, a first prism 221 having the rear end surface formed to be a slope and a second prism formed to be like a wedge are cemented in the order mentioned. The above mentioned second prism 222 is cemented to the slope at the rear end of the above mentioned first prism 221 so that the thin part may be on the tip side. On the sloped rear end surface of the above mentioned second prism 222, a solid state imaging device 225 is arranged so that the imaging surface may incline with respect to the lengthwise direction of the insertable part 202 and is fixed on a flexible substrate 226 fitted with electronic parts 227 and connected with signal wires 228 which are inserted through the above mentioned flexible tube 211, are extended out of the insertable part 202 at the base end and are led into the above mentioned drum 204. These signal wires 228 are inserted through one rotary shaft part through a slip ring (not illustrated) provided within the above mentioned drum 204, are inserted from one bearing part 206 into the handle 208 and are led out to the other bearing part 206. Further, these signal wires 228 are inserted through a signal wire cable 229 extended out of the side of the above mentioned bearing part 206 and are connected to a signal connector 230 provided at the end of this signal wire cable 229. This signal connector 230 is removably connected to the video processor 242 processing the signal from the above mentioned solid state imaging device 225.

A light distributing lens 231 is fitted to the above mentioned illuminating through hole 216. A light guide fiber bundle 232 is connected to this light distributing lens 231 at the rear end, is inserted through the above mentioned flexible tube 211, is extended out of the insertable part 202 at the base end and is led into the above mentioned drum 204. This light guide fiber bundle 232 is inserted through the rotary shaft part on the side on which the above mentioned signal wire cable 229 is extended, is extended out of the bearing part 206, is inserted through a flexible connecting cable 233 extended from the side of this bearing part 206 and is connected to a light source connector 234 provided at the end of this connecting cable 233. This light source connector 234 is removably connected to the above mentioned light source apparatus 241.

For example, in two places of the above mentioned tip part body 214, through an insulating member 235, for example, bar-like electric contacts 236 are fixed as by cementing in the lengthwise direction of the insertable part 202. These electric contacts 236 somewhat project at the tips from the tip surface of the above mentioned tip part body 214. Lead wires 237 are connected as by soldering to the above mentioned electric contacts 236 at the rear ends, are inserted through the above mentioned flexible tube 211, are extended out of the insertable part 202 at the base end and are led into the above mentioned drum 204. These lead wires 237 are connected to a connector 238 provided on the side of the bearing part 206 on the side on which the above mentioned signal wire cable 229 and light guide fiber bundle 232 are extended through, for example, a slip ring (not illustrated) provided within the above mentioned drum 204. A signal cable 239 connected to the above mentioned rotation controlling apparatus 244 is connected to this connector 238.

On the other hand, the above mentioned adapter 250 is provided with a substantially columnar adapter body 251 removably connected to the above mentioned tip part 212 on the tip side and a motor part 253 connected to this adapter body 251 on the front side, for example, through two pipe-like connecting members 252. The above mentioned connecting members 252 are arranged in the positions corresponding to the electric contacts provided in the above mentioned tip part body 214.

In the above mentioned adapter body 251, in the positions corresponding to the observing through hole and illuminating through hole of the above mentioned tip part body 214, an observing through hole 255 and illuminating through hole 256 are respectively formed parallelly in the lengthwise direction of the insertable part 202. A lens system forming an image forming optical system together with the above mentioned objective lens system 218 is fitted as partly held by a lens frame 257 in the above mentioned observing through hole 255.

In the above mentioned adapter body 251, electric contact housing parts 261 are provided in the positions communicating with the hollow parts of the above mentioned connecting members 252 and corresponding to the electric contacts 236 provided in the above mentioned tip part body 214. In this electric contact housing part 261, from the tip side, a substantially cylindrical first insulating member 262 and substantially tubular second insulating member 263 are, for example, cemented and fixed in the lengthwise direction of the insertable part 2. A substantially bar-like electric contact 264 is housed in these insulating members 262 and 263 and has an expanded diameter flange part 264a formed in the course in the axial direction to be arranged between the rear end surface of the first insulating member 262 and a step formed on the rear end side of the second insulating member 263. A spring 265 energizing the above mentioned electric contact 264 to the rear end side is arranged between the above mentioned flange part 264a and the rear end surface of the above mentioned first insulating member 262 so that, in case the above mentioned adapter body 252 is connected to the above mentioned tip part body 214, the above mentioned electric contact 264 will contact at the rear end with the electric contact 236 of the tip part body at the tip.

The above mentioned adapter body 251 is formed to be cylindrical on the rear end side and this cylindrical part 275 is externally fitted to the above mentioned tip part body 214. A female screw is formed in the rear end part of this cylindrical part 275. On the other hand, a connecting ring 276 is rotatably loosely fitted to the above mentioned tip part body 214 on the outer periphery and is provided on the tip side with a male screw screwed with the female screw of the above mentioned cylindrical part 275. By screwing these female screw and male screw with each other, the adapter body 251 is fixed to the tip part body 214.

The above mentioned motor part 253 is provided with a cylindrical motor case 266 closed on the rear end side and a lid body 267 closing the opening at the tip of this motor case 266. A motor 268 is housed within the above mentioned motor case 266. The rotary shaft 268a of this motor 268 is arranged parallelly in the lengthwise direction of the insertable part 2 and is projected rearward through the rear end surface of the above mentioned motor case 266. A cylindrical mirror 270 rotated by the above mentioned motor 268 is fitted to this rotary shaft 268a and is arranged forward on the optical axis of the lens system 258 of the above mentioned adapter body 251 in the space between the above mentioned adapter body 251 and the motor part 253. The reflecting surface 270a of this cylindrical mirror 270 is inclined, for example, by about 45 degrees to the lengthwise direction of the insertable part 202. The light of the visual field in the direction substantially vertical to the lengthwise direction of the insertable part 202, that is, in the sidewise direction enters the lens system 258 of the above mentioned adapter body 251 through the reflecting surface 270a of this cylindrical mirror 270. For example, two lead wires 271 connected to the above mentioned motor 268 are inserted through the hollow parts of the above mentioned connecting members 252 and are connected, for example, by soldering to the rear end parts of the electric contacts 264 of the above mentioned adapter body 251. The above mentioned motor 268 is connected to the rotation controlling apparatus 244 through the above mentioned lead wires 271, electric contacts 264 and 236, lead wires 237, connector 238 and signal cable 239, is fed with an electric power from this rotation controlling apparatus 244 and is controlled in the rotation. When this motor 268 rotates, the cylindrical mirror 270 will be rotated and the visual field direction of the lens system 258 of the above mentioned adapter body 251 will be converted.

In the case of the visual field convertible observation by using the adapter 250 formed as in the above, the light source connector 234 provided at the end of the connecting cable 233 is connected to the light source apparatus 241, the signal connector 230 provided at the end of the signal cable 229 is connected to the video processor 242 and the signal cable 239 connected to the rotation controlling apparatus 244 is connected to the connector 238. On the other hand, the adapter 250 is connected to the tip part 212 of the insertable part 202.

The illuminating light emitted from the above mentioned light source apparatus 241 enters the entrance end of the light guide fiber bundle 232 of the above mentioned light source connector 234, is led to the tip part 212 through the light guide fiber bundle 232, is emitted from the tip surface and is radiated to an object through the light distributing lens system 259 of the adapter body 251.

The light returning from the object by this illuminating light is reflected by the reflecting surface 270a of the cylindrical mirror 270, enters the lens system 258 of the adapter body 251 and is made to form an image on the solid state imaging device 225 by the objective lens system 218 of the tip part body 214. The output signal of this solid state imaging device 225 is input into the video processor 242 through the signal wire 228, slip ring (not illustrated) within the drum 204, signal wire within the signal cable 229 and signal connector 230 and is processed to be a video signal by this video processor. The video signal produced by this video processor 242 is input into the monitor 243 and an observed image is displayed in this monitor 243.

Also, by connecting the adapter body 251 of the above mentioned adapter 250 to the tip part body 214, the electric contact 236 of the tip part body 214 and the electric contact 264 of the adapter body 251 are electrically connected with each other. The motor 268 of the above mentioned adapter 250 is connected to the rotation controlling apparatus 244 through the lead wires 271, electric contacts 268 and 236, lead wires 237, connector 238 and signal cable 239, is fed with an electric power from this rotation controlling apparatus 244 and is controlled in the rotation. By the rotation of this motor 268, the cylindrical mirror 270 is rotated and the visual field direction, that is, the observed visual field direction of the lens system 258 of the above mentioned adapter body 251 is converted. For example, by rotating the above mentioned motor 268 at a predetermined speed, the sidewise visual field of the insertable part 202 can be continuously observed while being varied to be in the peripheral direction. By stopping the above mentioned motor 268 in any position, the visual field can be observed as fixed in any visual field direction.

Thus, according to this embodiment, as the lead wire 237 for feeding an electric power to the motor 268 of the adapter 250 is inserted through the insertable part 202 and is connected with the lead wire 271 of the motor 268 through the electric contacts 236 and 264 provided in the tip part body 214 and adapter body 251, the lead wire for feeding an electric power to the motor 268 is not exposed out of the insertable part 202 and is not likely to be broken, the insertability of the insertable part 202 is not impaired and the lead wire is not in the way to impair the housability of the adapter 250. Further, as the rotation controlling apparatus 244 feeding an electric power to the motor 268 and controlling the rotation is provided separately from the adapter 250, the operator can simply control the visual field conversion on the hand base side.

A cylindrical transparent cover may be provided between the adapter body 251 and motor part 253 to protect the cylindrical mirror 270.

Figure 13:
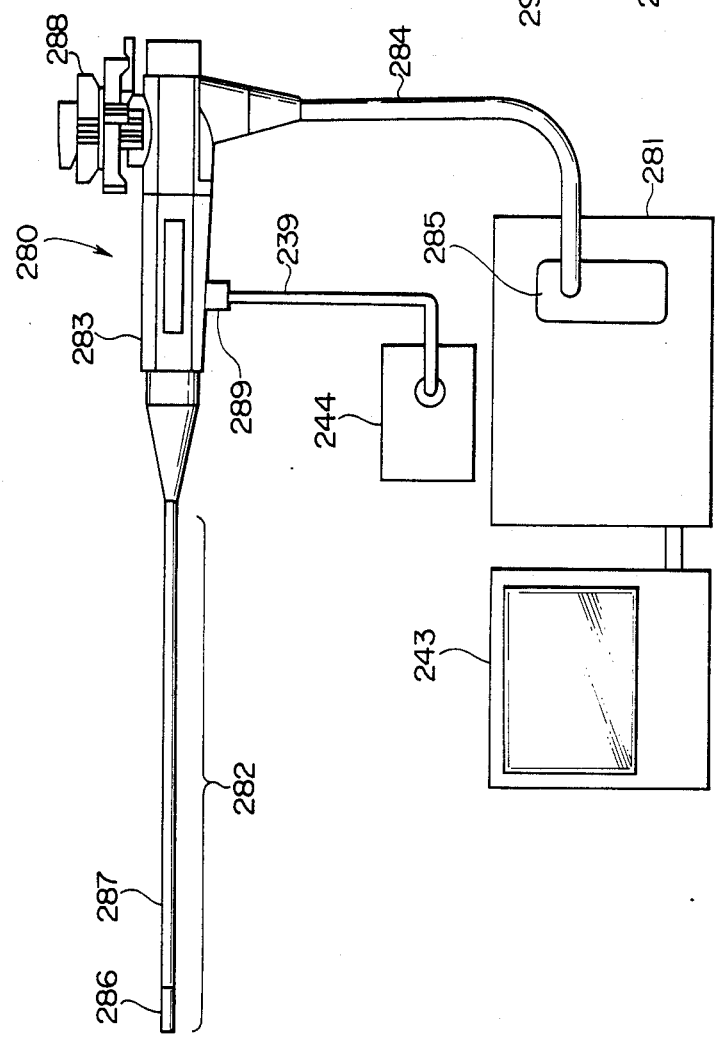

FIG. 13 is an explanatory view of an endoscope apparatus fitted with a rotary type visual field converting adapter.

In FIG. 13, the endoscope apparatus is provided with an electronic endoscope apparatus 280, a video processor 281 containing a light source apparatus and video signal processing circuit, a monitor 243 connected to this video processor 281 and a rotation controlling apparatus 244. The above mentioned endoscope 280 is provided with an elongate and, for example, flexible insertable part 282, a thick operating part 183 connected to this insertable part 282 at the rear end and a universal cord 284 extended sidewise from this operating part 283. The above mentioned universal cord 284 is provided at the end with a connector 285 removably connectable to the above mentioned video processor 281. The above mentioned insertable part 282 is provided on the tip side with a rigid tip part 286 an a curvable part 287 connected to this tip part 286 on the rear side. The above mentioned operating part 283 is provided with a curving operation knob 288 curving the above mentioned curvable part 287 and a connector 289 to which a signal cable 239 connected to the above mentioned rotation controlling apparatus 244 can be removably connected.

The formation of the above mentioned insertable part 282 is the same as of the insertable part 202 in FIGS. 11 and 12. That is to say, a light guide fiber bundle 232 is inserted through the above mentioned insertable part 202, is inserted on the base side through the above mentioned universal cord 284 and is connected to the above mentioned connector 285. An illuminating light from a light source apparatus (not illustrated) within the above mentioned video processor 281 connected through this connector 285 enters the light guide fiber bundle 232. Also, the above mentioned tip part 286 is provided with an objective lens system 218 and a solid state imaging device 225 arranged in the image forming position of this objective lens system 218. Signal wires 228 connected to this solid state imaging device 225 are inserted through the above mentioned insertable part 282, operating part 283 and universal cord 284, are connected to the above mentioned connector 285 and are connected to the video signal processing circuit within the video processor through this connector 285.

The same as in FIGS. 11 and 12, a rotary type visual field converting adapter 250 is removably fitted to the above mentioned tip part 286. A lead wire 237 connected to an electric contact 236 provided in this tip part 286 is inserted through the above mentioned insertable part 282 and is connected to a connector 289 provided on the above mentioned operating part 283.

The other formations, operations and effects are the same as in FIGS. 11 and 12.

In the above mentioned FIGS. 11 to 13, the drum 204 or operating part 283 is provided with the connectors 238 and 289 and is connected with the rotation controlling apparatus 244 through these connectors 238 and 289. However, for example, the function of the rotation controlling apparatus 244 may be contained in the light source apparatus 241 or video processors 242 and 281. The lead wires 237 connected to the electric contacts 236 may be inserted through the connecting cable 233, signal wire cable 229 or universal cord 284 and may be connected directly to the light source apparatus 241 or video processors 242 and 281.

Figure 15:
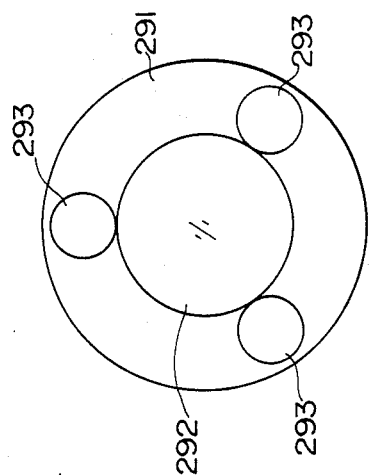
Figure 14:
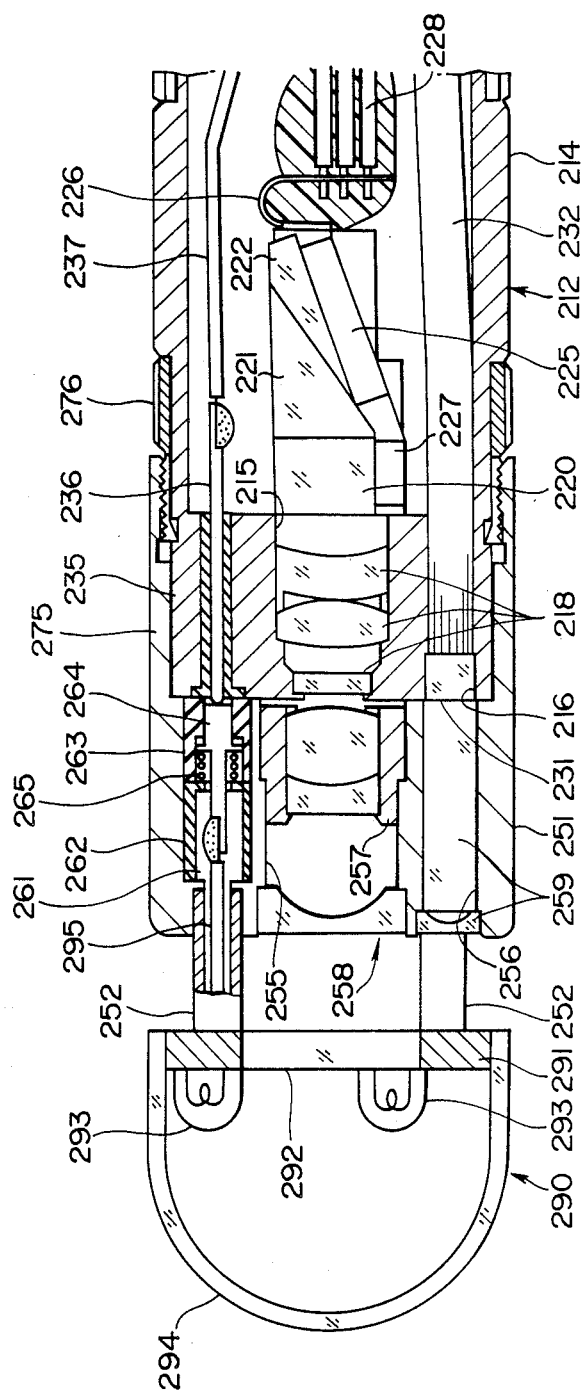

In FIGS. 14 and 15, an auxiliary light source adapter 290 is removably fitted to the tip part 212 of the insertable part 202 of the same formation as in FIGS. 11 and 12.

In the above mentioned auxiliary light source adapter 290, a disk-like substrate 291 is connected through connecting members 252 in front of the adapter body 251 in the first embodiment. This substrate 291 is incised, for example, circularly in the central part and is fitted with a transparent plate 292. On the front surface of the above mentioned substrate 291, as shown in FIG. 15, for example, three lamps 293 are fitted in the peripheral direction and are covered with substantially hemispherical transparent cover members 294 fitted to the front surface side of the above mentioned substrate 291. Electric power feeding lead wires 295 connected to the above mentioned lamps 293 are inserted through the hollow parts of the above mentioned connecting members 252 and are connected, for example, by soldering to electric contacts 264 of the adapter body 251.

According to the above mention, the lead wires 237 connected to the electric contacts 236 of the tip part body 214 connected with the above mentioned electric contacts 264 are connected to a power source (not illustrated) feeding an electric power to the above mentioned lamps 293 instead of the rotation controlling apparatus 244. The above mentioned lamps 293 are fed with an electric power from the above mentioned power source and emit auxiliary illuminating lights.

In FIGS. 14 and 15, by making the power source feeding the electric power to the above mentioned lamps 293 a control apparatus which can control the brightness of the lamps 293, the brightness of the auxiliary illuminating light can be controlled on the hand base side.

The present invention is not limited to the above mentioned respective embodiments. For example, the function of the adapter fitted to the tip part of the insertable part is not limited to the picture angle conversion, rotary type visual field conversion and auxiliary illuminating light.

For example, a zooming adapter provided with a zoom lens and driving means moving this zoom lens may be provided and the tip part and adapter may be provided with electric contacts for drive controlling signals for the above mentioned driving means.

Also, a treating adapter provided with a holding arm and a driving means driving this arm may be provided and the tip part and adapter may be provided with electric contacts for drive controlling signals for the above mentioned driving means.

Also, an adapter having various kinds of sensors may be provided and the tip part and adapter may be provided with electric contacts for transmitting signals from the above mentioned sensors to an apparatus on the tip side.

Also, an adapter having running wheels automatically advancing the tip part within a tube or the like may be provided and the tip part and adapter may be provided with electric contacts for drive controlling signals for the above mentioned running wheels.

Further, the above mentioned tip part may be provided with a plurality of kinds of electric contacts corresponding to a plurality of kinds of adapters so as to be interchangeably fitted with such various kinds of adapters as are described above and may be selectively used in response to the adapter.

What is claimed is:

1. An endoscope including:
   a flexible insertable part;
   a solid state imaging device obtaining an optical image of an observed part through an observing window provided in a tip part of said insertable part; and
   signal wires inserted through said insertable part, electrically connected to said solid state imaging device and said signal wires having parts with higher flexibility than other parts thereof in a lengthwise direction.

2. An endoscope according to claim 1 wherein further said insertable part is provided in a rear of said tip part with a curvable part curving to direct said tip part in a predetermined direction.

3. An endoscope according to claim 2 wherein said signal wires are made higher in flexibility in a part inserted through said curvable part than in other parts.

4. An endoscope according to claim 3 wherein said signal wires are shielding wires coated on an outer periphery with an external conductor.

5. An endoscope according to claim 4 wherein said external conductor is knitted of fine wires formed of an electric conductive material and is knitted in one layer within said curvable part and is knitted in two layers in the other parts.

6. An endoscope according to claim 4 wherein said external conductor is knitted of fine wires formed of an electric conductive material and is more coarsely knitted within said curvable part than in the other parts.

7. An endoscope according to claim 4 wherein said shielding wires consist of a first shielding wire inserted through said curvable part and a second shielding wire inserted through the other parts electrically connected with each other and knitting density of the external conductor of the first shielding wire is lower than knitting density of the external conductor of the second shielding wire.

* * * * *